United States Patent
Hensel

(10) Patent No.: US 6,822,215 B2
(45) Date of Patent: Nov. 23, 2004

(54) OPTOELECTRONIC SENSOR INCLUDING A TRANSPARENT OPTODE MATERIAL

(75) Inventor: Andreas Hensel, Vaihingen (DE)

(73) Assignee: Robert Bosch GmbH, Stuttgart (DE)

( * ) Notice: Subject to any disclaimer, the term of this patent is extended or adjusted under 35 U.S.C. 154(b) by 259 days.

(21) Appl. No.: 10/018,203

(22) PCT Filed: Mar. 24, 2001

(86) PCT No.: PCT/DE01/01148

§ 371 (c)(1),
(2), (4) Date: May 7, 2002

(87) PCT Pub. No.: WO01/79819

PCT Pub. Date: Oct. 25, 2001

(65) Prior Publication Data

US 2002/0148948 A1 Oct. 17, 2002

(30) Foreign Application Priority Data

Apr. 14, 2000 (DE) .......................................... 100 18 550

(51) Int. Cl.$^7$ ........................... G01J 1/04; G01N 21/00; G02B 6/00
(52) U.S. Cl. ............................. 250/214.1; 250/227.14; 385/12; 385/141; 422/82.06; 422/83
(58) Field of Search .......................... 250/214.1, 227.14; 356/432–437; 385/12, 14, 141, 142, 143; 422/82.05, 82.06, 82.09, 83; 436/136

(56) References Cited

U.S. PATENT DOCUMENTS

| 5,039,491 A | 8/1991 | Saaski et al. |
| 5,822,473 A | 10/1998 | Magel et al. |
| 6,704,470 B1 * | 3/2004 | Schneider et al. ............ 385/12 |

FOREIGN PATENT DOCUMENTS

| DE | 198 35 769 | 2/2000 |
| DE | 198 45 553 | 4/2000 |
| EP | 0 903 573 | 3/1999 |

\* cited by examiner

Primary Examiner—Stephone B. Allen
(74) Attorney, Agent, or Firm—Kenyon & Kenyon

(57) ABSTRACT

An optoelectronic sensor, which is based on optodes and with which, thanks to optode material that has been rendered reflective, virtually any angle for injecting the light into the optode material is feasible, is proposed. Thus, advantageously, a longer optical path is achieved than would be feasible in the case of total reflection. Thus greater measuring precision can be achieved. In the present case the optode material is a polymer, reflectivity being provided by introducing metal particles into the polymer. The light emitter and the light-sensitive sensors are an LED and photodiodes respectively. A plurality of optoelectronic sensors can be combined to form a gas sensor array.

18 Claims, 1 Drawing Sheet

OPTOELECTRONIC SENSOR INCLUDING A TRANSPARENT OPTODE MATERIAL

FIELD OF THE INVENTION

The present invention relates to an optoelectronic sensor.

BACKGROUND INFORMATION

In the case of optodes used in fire alarm systems, there are various different ways to implement optical measuring systems. One approach is Multiple Internal Reflection/Attenuated Total Reflection (MIRE/ATR), which involves injecting light into a highly refractive material so that the light undergoes total reflection, a membrane having been deposited on the highly refractive material so that the evanescent field of the light that has been injected is absorbed by the membrane. If the membrane comes into contact with an analyte—a gas to be measured—the membrane'absorption and thus absorption of the light changes. Thus by measuring the absorption it is possible to measure the concentration of the gas to be measured, because the membrane changes its absorption characteristics based on the concentration of the gas. Herein, one necessary condition is that only the evanescent field penetrates into the membrane and is absorbed.

Another measuring method is transmission measurement. In this case too, changes in absorption are measured. Herein, light passes through a membrane that comes into contact with the analyte, absorption by the membrane changing as a function of the analyte. By carrying out comparison measurements with and without the analyte, it is possible to determine the analyte. If necessary a rinsing solution can be used to remove the analyte from the membrane between measurements.

SUMMARY OF THE INVENTION

By contrast, the optoelectronic sensor according to the present invention has the advantage that the light does not have to be injected into the optode causing total reflection, so that the light can be injected into the optode at any angle desired, as the optode has a mirror that reflects the light on the edge of the optode back into the optode. As a result, greater angles can be used for injecting the light, so that the optical path through the optode from the light emitter to the light-sensitive sensors is longer than if only the angles for total reflection were used. Thus the measuring sensitivity is greater, as the interaction of the light with the optode is possible over a longer path. The measurement regarding the gas, which is to be analyzed and which penetrates the optode, can be determined immediately via the light-sensitive sensors.

This increased measuring sensitivity can be used advantageously to simply and quickly spot the early stages of jaundice in babies, the carbon monoxide content of the baby's exhaled breath being analyzed. If the carbon monoxide content exceeds 1.8 ppm, this indicates that the baby may possibly have jaundice. The optoelectronic transmitter according to the present invention supplies a measurement immediately, so that timely, life-saving treatment can be provided.

It is especially advantageous that the mirror is created on the outside of the optode material via metallic particles that are introduced. This method is straightforward and can easily be integrated into the production process for the optoelectronic sensor.

Furthermore it is advantageous that covering the optode material with an opaque material keeps light from exiting via scattered light. This reduces the effect of scattered light on the measurement being carried out, and thus increases the precision of the measurement.

Furthermore, it is advantageous that the optode material is a polymer to which an indicator substance is added. Using a polymer along with an indicator substance makes it easier to produce the optode material and apply it to the semiconductor substrate.

Furthermore, it is advantageous that pigment molecules are present in the indicator substance and result in gas-dependent absorption of the light that is injected. It is advantageous that these pigment molecules allow reversible, gas-type-dependent absorption, which is then used to determine the gas concentration via the absorption that is measured.

Furthermore, it is advantageous that the opaque material is embodied as a polymer, which means the production process for this opaque layer can be tailored to the production process for the optodes. Thus the production process as a whole can be simplified.

Furthermore, it is advantageous that the light-sensitive sensors having the sections of the optode material that cover them are arranged as sectors and rotationally symmetrically around the light emitter. Thus the light emitted by the light emitter is distributed evenly and used to carry out measurement in the various sections that are covered by the optode material.

A chip that forms the optoelectronic sensor can thus be embodied as square, as having 5, 6, 7, or 8 corners, or as circular. In addition, an optoelectronic sensor of this kind may also include fewer than or more than four transmission branches.

Furthermore, it is advantageous that the semiconductor substrate is formed from n-type silicon, and the light-sensitive elements are formed from p-type silicon areas that are integrated into the n-type silicon substrate. In this way the light-sensitive elements form photodiodes. The light emitter is preferably an—LED; it is also possible to provide a plurality of LEDs to define the wavelength.

Furthermore, it is advantageous that the optode material is designed to detect nitrogen oxides, so that these gases that characterize a fire can be detected quantitatively by the fire alarm having the optoelectronic sensor. Thus, on the basis of the high degree of measuring sensitivity of the optoelectronic sensor according to the present invention, fires can be detected early.

Furthermore, it is advantageous that the sensor according to the present invention has an oxidation material provided on a carrier material to keep the sensor according to the present invention from being damaged by sulfur dioxide. Alternatively, it is possible for the sensor according to the present invention to have a molecular sieve that filters out undesired gases.

In the optoelectronic sensor the individual transmission branches are separated by barriers so that the individual transmission branches do not influence each other optically due to scattered light exiting from the optode material. The height of these barriers may be roughly equal to the height of the central light sensor. In addition, all parts of the chip that are not light sensitive may, if necessary, be rendered reflective, this including the sidewalls of the barriers. To accomplish this, it is advantageous to carry out metallization, preferably using gold.

Furthermore, it is advantageous that the light emitter is operated using pulses, so that the power consumption of the sensor according to the present invention is reduced.

By combining a plurality of optoelectronic sensors to form a sensor array, a high degree of measuring precision can be achieved, and large attack surfaces for the gas to be detected can be provided. To accomplish this, the optoelectronic sensor according to the present invention has conductors, some of which supply power to the light emitter and the light sensitive sensors, while others pick off the measurement signals.

DETAILED DESCRIPTION

Optoelectronic sensors, in particular if they are produced using semiconductors, have the advantage that their dimensions are very small. If an optode material through which the light is beamed so that a gas concentration can be determined quantitatively based on the absorption in the optode material is used, the mutual interaction of the gas with the optode material, i.e., the absorption of the light, is a function of the distance that the light has traveled through the optode material. The greater the length of the path, the more frequently the light is attenuated via gas-dependent absorption by the optode material. Therefore an important goal is to increase the length of the light path in an optode material. Total reflection in an optode material, e.g., a polymer, only permits a specific angle at which the light is at least injected so that the light does not exit from the optode. Steeper angles that result in a longer optical path do not observe the angle for total reflection, and the light couples out of the optode.

Therefore, according to the present invention a mirror is provided on the outer edge of the optode material so that virtually any angle for injecting the light, and thus longer optical paths covered by the light as it passes through the optode material, are feasible. An indicator substance having pigment molecules is provided in the optode material. The optode material itself is a polymer carrier material which has at least one indicator substance from the group of compounds that includes azobenzenes, acetophenones, corrins, porphyrins, phthalocyanins, macrolides, porphyrinogens, nonactins, valinomycins and/or complexes thereof with transition metals of the first, second and fifth to eighth subgroups. These substances result in a reversible change in the absorption characteristics under the influence of gases to be detected, e.g., nitrogen oxides or carbon monoxide. Furthermore, other substances such as amines, water vapor, oxygen, or alcohols can also be identified with the help of these indicator substances. Chromoionophores, which result in a color change and thus a change in the absorption behavior when they come into contact with a gas to be detected, are present.

Figure 1:
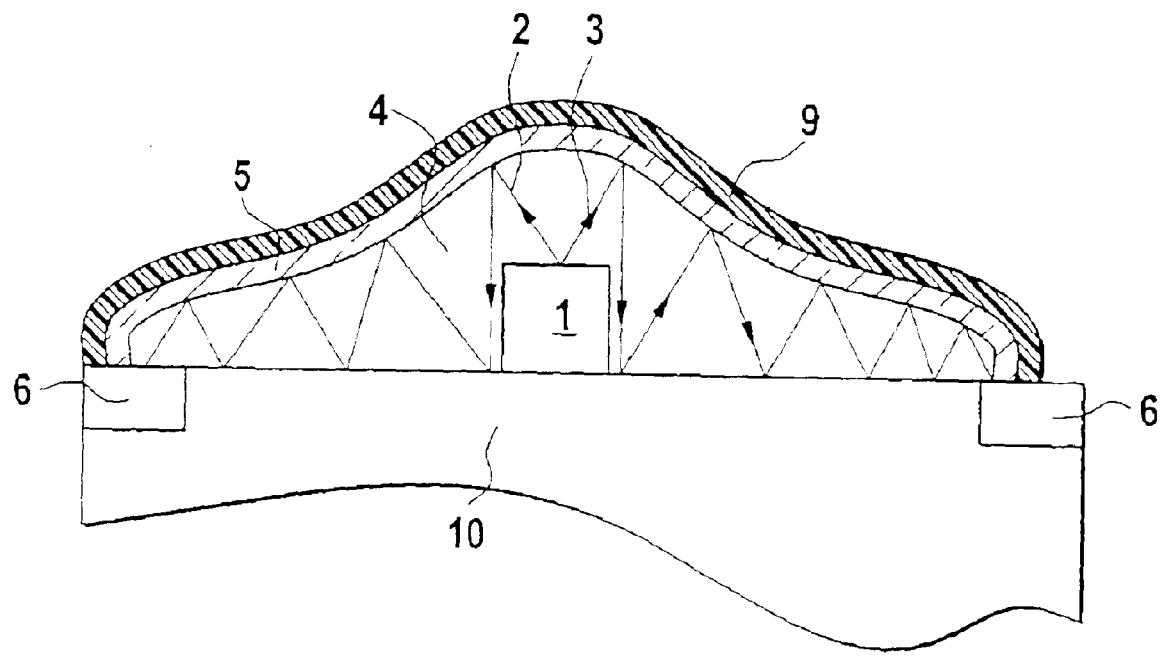
FIG. 1 is a cross section through the optoelectronic sensor according to the present invention, this being schematically shown.

FIG. 1 shows a cross section through an optoelectronic sensor according to the present invention, this being schematically shown. Light emitter 1 is located in the center. Light emitter 1 is in this case a light-emitting diode (LED). Alternatively a laser diode or small lamps or other light sources may be used. Two light beams 2 and 3 which exit light emitter 1 are shown for representation purposes. Here we will only describe the geometric optics. In actuality, light emitter 1 emits light beams at many other angles. In the present case the light emitter is operated by electrical pulses so as to reduce power consumption. As a result, only light pulses are sent. Using pulses not only reduces power consumption, but also has the advantage that thermal effects have a reduced impact. A suitable frequency for the pulses is chosen based on the light emitter used.

Light beams 2 and 3 strike the outer edge of optode material 4, which is located on light emitter 1, semiconductor substrate 10 and light-sensitive sensors 6, at an angle that is smaller than the angle required for total reflection. Thus the optical path of light beams 2 and 3 is longer than it would be if they were injected into optode material 4 under the conditions for total reflection. As optode material 4 is located directly on light emitter 1; this guarantees direct overcoupling of the light.

As explained above, in the present case optode material 4 is a polymer having the aforementioned indicator substances. An optode is an optical sensor. In the present case optode material 4 is embodied as an optical waveguide through which light is conducted, absorption of the light by this optical waveguide being determined by a gas concentration. By selecting the various indicator substances in an appropriate manner, the absorption behavior can be set as required for different gases, e.g., carbon monoxide or nitrogen oxides.

In the present case, optode material 4 is also referred to as a membrane, as it is applied as such to light emitter 1, semiconductor substrate 10 and light-sensitive sensors 6. To keep light from exiting from optode material 4, mirror 5 is provided on optode material 4. Mirror 5 reflects the beams back into optode material 4. In the present case mirror 5 is created by introducing metal particles into the polymer for optode material 4. Alternatively, a metal film may be deposited on optode material 4 via vapor deposition, it also being possible to apply a metal film via a coating method.

Because, to create the mirror, metal particles are introduced into the polymer of optode material 4, creation of the mirror can be carried out in conjunction with application of the optode material. The polymer of optode material 4 is applied in a liquid state to optical waveguide 1, semiconductor substrate 10, and light-sensitive sensors 6. The polymer is rendered solid via drying and/or heating. A further polymer, namely opaque layer 9, is provided on mirror 5. Opaque layer 9 blocks off light that has not been reflected back into optode material 4 by mirror 5, so that scattered light that exits does not render the gas concentration measurements inaccurate. Opaque layer 9 is embodied so that it is inert relative to optode material 4, i.e., it does not undergo any reaction with it or change its characteristics.

Optode material 4 is rounded off at the end next to light-sensitive sensors 6 so that the light is injected more effectively into the light-sensitive sensors.

LED 1 as the light emitter is produced either by diffusing dopants into it or by mounting LED 1 on semiconductor substrate 10. Moreover, light-sensitive sensors 6 are also created by diffusing in dopants at the points where light-sensitive sensors 6 are to be created. The components are then created via standard silicon semiconductor technology process steps, e.g., photolithography, etching, passivation, or metallization. In the present case n-type silicon is present as semiconductor substrate 10. In order to create photodiodes as light-sensitive sensors 6, acceptors are diffused into it at the points where light-sensitive sensors 6 are to be created. Because in the present case silicon is involved, boron can be used as an acceptor. It is also feasible to implant the acceptors.

Instead of using silicon, it is also feasible to use compound semiconductors which may be more suitable for light-emitting components. Compound semiconductors of this kind include arsenides, phosphides, nitrides, antimonides, and silicon carbide.

Opaque polymer 9, mirror 5, and optode material 4 are permeable to the gas to be measured.

Figure 2:
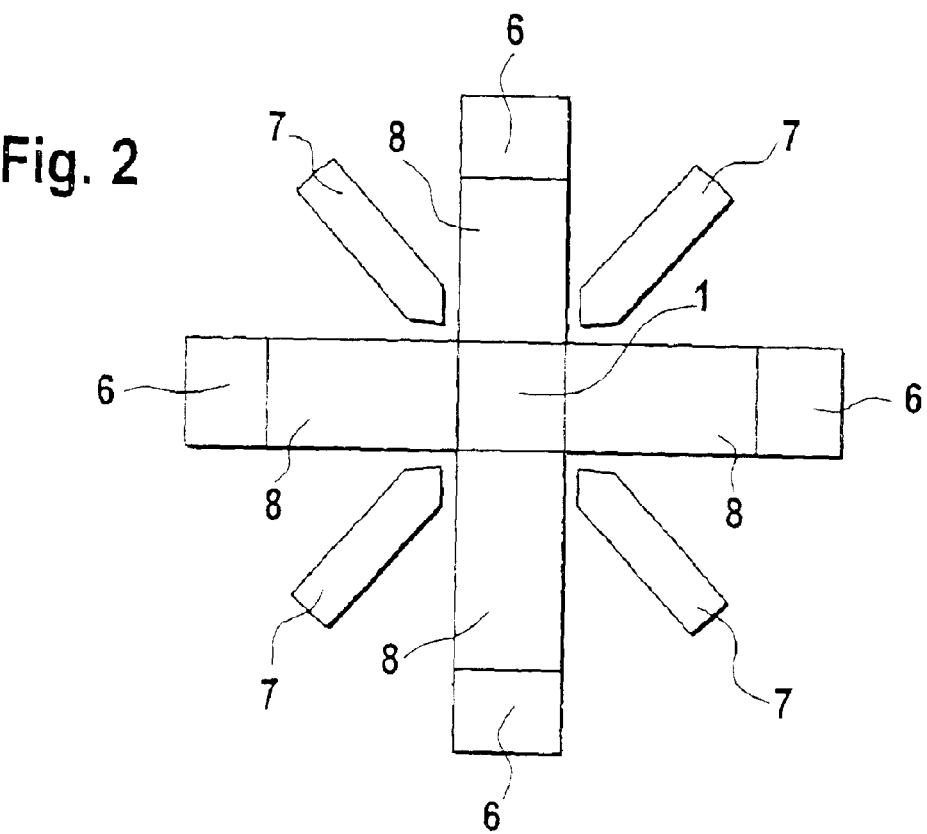
FIG. 2 is a top view of the optoelectronic sensor according to the present invention, this being schematically shown.

FIG. 2 shows a top view of the optoelectronic sensor according to the present invention, this being schematically shown. Light emitter 1 is located centrally, at the center of the sensor. The respective transmission arms 8 lead from light emitter 1 to light-sensitive sensors 6. Barriers 7 are located between transmission arms 8 to prevent cross-pickup caused by scattered light. Alternatively, more than four transmission arms may be used, it also being feasible to use fewer transmission arms.

Because the light emitted by light emitter 1 is distributed evenly, optimal use can be made of the surface of the optoelectronic sensor. Transmission arms 8, which form the membrane of the optode material, are 600 to 1200 micrometers in length, 280 micrometers wide, and have a thickness of 10 micrometers. The distance between light emitter 1 and light-sensitive sensors 6 should be as small as possible, in order to keep the maximum luminous power to be applied to a minimum. This also saves chip surface area. If the dimensions indicated are used, according to the present invention the optical path is maximized.

Barriers 7 may be made of semiconductor material that has no electrical function when insulated. In addition, a metal layer may be applied to barriers 7 in order to reflect scattered light. Alternatively, barriers 7 may be made of metal or a dielectric material. As barriers 7 are used to prevent cross pickup between the transmission arms, the height of barriers 7 is at least equal to that of LED 1.

A sensor field—known as a sensor array—can be created by combining a plurality of optoelectronic sensors according to the present invention that are produced on the semiconductor substrate. As a result, measurements can be taken using a plurality of sensors simultaneously so that a stronger measuring signal can be obtained, as a larger total area is covered by optode material and used for evaluation. Light emitter 1 and light-sensitive sensors 6 are supplied by central voltage and current sources. The output signals from light sensors 6 that carry the measured signals are sent to amplifiers. To ensure better evaluation, the measured signals are amplified by the amplifiers, which are connected to the optoelectronic sensors according to the present invention.

As the optoelectronic sensor can also be used in a fire alarm, preferably nitrogen dioxide and/or carbon monoxide and/or carbon dioxide being detected as the gases that indicate a fire; the sensor is herein also protected against harmful gases. A harmful gas of this kind is, in particular, sulfur dioxide. Sulfur dioxide would irreversibly damage the optode material. In order to separate sulfur dioxide from the gases to be measured, e.g., CO or $CO_2$, use is made of the fact that $SO_2$ can be oxidized to form $SO_3$. Sulfur trioxide no longer presents a problem as a harmful gas. In this case potassium permanganate is used as the oxidation material. Other oxidation materials such as chromates may also be used.

Another option for separating $CO_2$ from $SO_2$ is to use a molecular sieve. As $CO_2$ and $SO_2$ differ considerably in terms of their spatial structure, they are adsorbed differently by the molecular sieve. A molecular sieve has an arrangement that includes tubes which are coated with an oxidation material on their inside walls.

What is claimed is:

1. An optoelectronic sensor based on optodes, comprising:
    a semiconductor substrate;
    a plurality of separate light-sensitive sensors arranged on the semiconductor substrate;
    a light emitter located in a center of the semiconductor substrate; and
    a transparent optode material covering the light emitter and the plurality of separate light-sensitive sensors, wherein:
        the transparent optode material is reflective on a side that faces away from the semiconductor substrate.

2. The optoelectronic sensor according to claim 1, further comprising:
    metal particles arranged into the transparent optode material and by which a reflectivity is created.

3. The optoelectronic sensor according to claim 1, wherein:
    the semiconductor substrate is an n-type silicon substrate, and
    the plurality of separate light-sensitive sensors are made of p-type silicon.

4. The optoelectronic sensor according to claim 1, wherein:
    the plurality of separate light-sensitive sensors form photodiodes, and the light emitter is an LED.

5. The optoelectronic sensor according to claim 1, wherein:
    the transparent optode material detects one of a nitrogen oxide and carbon monoxide.

6. The optoelectronic sensor according to claim 1, further comprising:
    a molecular sieve.

7. The optoelectronic sensor according to claim 1, wherein:
    the light emitter can be operated by an electrical pulse.

8. The optoelectronic sensor according to claim 1, wherein the optode material is rounded-off at an end next to the plurality of separate light-sensitive sensors.

9. The optoelectronic sensor according to claim 1, further comprising:
    a plurality of barriers arranged between transmission branches.

10. The optoelectronic sensor according to claim 9, wherein at least one of the plurality of barriers includes a metal layer.

11. The optoelectronic sensor according to claim 9, wherein at least one of the plurality of barriers includes a dielectric material.

12. An optoelectronic sensor based on optodes, comprising:
    a semiconductor substrate;
    a plurality of separate light-sensitive sensors arranged on the semiconductor substrate;
    a light emitter located in a center of the semiconductor substrate;
    a transparent optode material covering the light emitter and the plurality of separate light-sensitive sensors, wherein the transparent optode material is reflective on a side that faces away from the semiconductor substrate; and
    an opaque material covering the transparent optode material.

13. The optoelectronic sensor according to claim 12, wherein:

the opaque material is a polymer.

14. The optoelectronic sensor according to claim 12, wherein:

the plurality of separate light-sensitive sensors are arranged as sectors and rotationally symmetrically around the light emitter.

15. An optoelectronic sensor based on optodes, comprising:

a semiconductor substrate;

a plurality of separate light-sensitive sensors arranged on the semiconductor substrate;

a light emitter located in a center of the semiconductor substrate; and a transparent optode material covering the light emitter and the plurality of separate light-sensitive sensors, wherein the transparent optode material is reflective on a side that faces away from the semiconductor substrate, wherein the transparent optode material is a polymer to which an indicator substance is added.

16. The optoelectronic sensor according to claim 15, wherein:

the indicator substance includes pigment molecules.

17. An optoelectronic sensor based on optodes, comprising:

a semiconductor substrate;

a plurality of separate light-sensitive sensors arranged on the semiconductor substrate;

a light emitter located in a center of the semiconductor substrate;

a transparent optode material covering the light emitter and the plurality of separate light-sensitive sensors, wherein the transparent optode material is reflective on a side that faces away from the semiconductor substrate; and an oxidation material provided on a carrier material.

18. A gas sensor array, comprising:

a plurality of array elements, each array element corresponding to an optoelectronic sensor based on optodes, the optoelectronic sensor including:

a semiconductor substrate, a plurality of separate light-sensitive sensors arranged on the semiconductor substrate, a light emitter located in a center of the semiconductor substrate, and a transparent optode material covering the light emitter and the plurality of separate light-sensitive sensors, wherein the transparent optode material is reflective on a side that faces away from the semiconductor substrate.

* * * * *